United States Patent [19]

Barry

[11] Patent Number: 4,636,082

[45] Date of Patent: Jan. 13, 1987

[54] FIBER OPTIC REFLECTANCE MEASUREMENT APPARATUS

[75] Inventor: Jürgen Barry, Munich, Fed. Rep. of Germany

[73] Assignee: Compur-Electronic GmbH, Fed. Rep. of Germany

[21] Appl. No.: 510,460

[22] Filed: Jul. 1, 1983

[30] Foreign Application Priority Data

Jul. 14, 1982 [DE] Fed. Rep. of Germany ....... 3226371

[51] Int. Cl.⁴ .......................................... G01N 21/47
[52] U.S. Cl. .................................... 356/446; 250/227
[58] Field of Search ................................ 356/445, 446

[56] References Cited

U.S. PATENT DOCUMENTS 3,806,256  4/1974  Ishak ................................... 356/446
4,033,698  7/1977  Demsky et al. ..................... 356/446
4,101,222  7/1978  Mathisen ......................... 356/446 X
4,464,054  8/1984  Karras et al. ................... 356/446 X

OTHER PUBLICATIONS

O'Donovan et al, "Proximal Scanning Systems: Improved Resolution Using Inclined Optical Fibers", Applied Optics, vol. 15, #5, May 76, 1299–1303.

*Primary Examiner*—Vincent P. McGraw
*Attorney, Agent, or Firm*—Townsend and Townsend

[57] ABSTRACT

To be certain of an even illumination of a field of measurement for measuring reflectance and to make it possible to have reflectance measuring heads of small size, the said field is illuminated with a number of discrete beams coming from transmitters, whose emission faces or areas are placed in a plane that is parallel to the plane of the said field. Preferably light guide cables are used for the transmitters and receivers.

12 Claims, 1 Drawing Figure

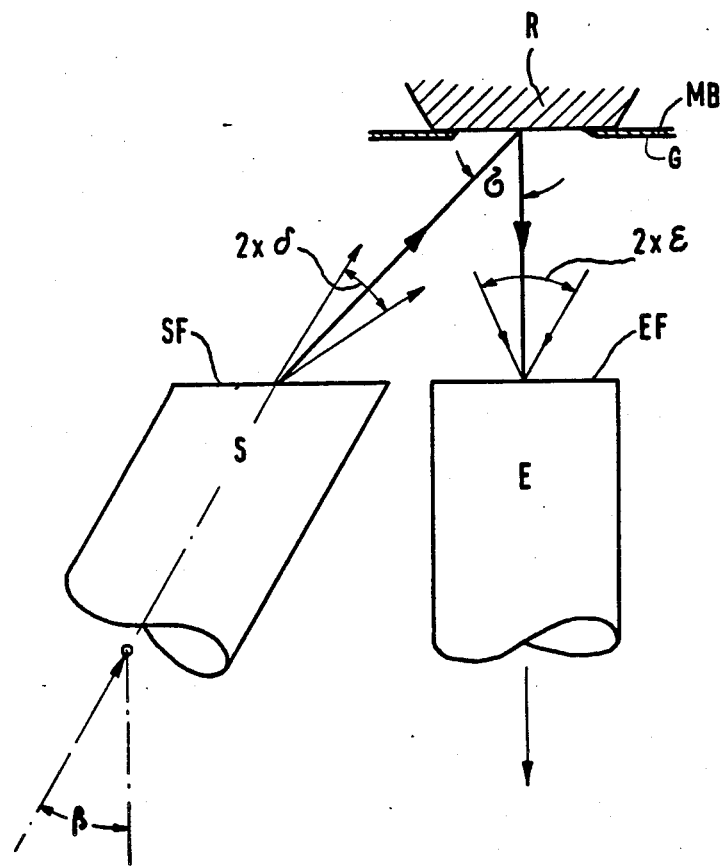

FIBER OPTIC REFLECTANCE MEASUREMENT APPARATUS

BACKGROUND OF THE INVENTION

The present invention is with respect to an apparatus for measuring reflectance at a reflecting surface placed in a field of measurement, using a transmitter and receiver.

Apparatus on these lines has been designed for measuring reflectance at light reflecting surfaces, for measuring the reflectance values and for detecting and measuring changes in reflectance quantitatively. In known apparatus using only one transmitter illuminating the field of measurement with only one single beam, for example at an angle of 45°, the lengths of the paths of the light from the light source to the different points in the field of measurement are different in length. Because the intensity of illumination is a function of the square of the path of the illuminating light, the field of measurement is not evenly illuminated so that there will in fact be different intensities of illumination at the different single points in the field of measurement. It is because of this inhomogeneous illumination of the field of measurement that different readings will be produced for the reflecting points in the field of measurement so that the measurements and readings for the reflectance will not be true. Seeing that the separate points of the field of measurement have to be acted upon by a given intensity of radiation, relatively high-intensity sources of radiation are needed that have an undesired heating or thermal effect on the sample. To put an end to such overgreat thermal effects on the sample, the radiating light source has to be kept at some distance from the field of measurement and may not be placed at any desired short distance therefrom so that the reflectance measuring apparatus has to be of a certain size and for this reason the degrees of freedom when designing the measuring apparatus are limited.

SUMMARY OF THE INVENTION

This being the case, one purpose of the present invention is that of designing an apparatus for measuring reflectance in the case of which the separate points within the field of measurement are evenly illuminated and for this reason may be equally measured and readings therefrom equally processed.

A still further purpose of the invention is that of designing such a reflectance measuring apparatus that is of small size without producing overly great heating effects in the field of measurement.

For effecting these purposes and further purposes that will come to mind on reading further parts of the present specification, the field of measurement is illuminated with a number of discrete beams coming from transmitters, whose emission areas or faces are placed in a plane that is parallel to the plane of the field of measurement.

Because the field of measurement is illuminated with a number of discrete beams or pencils of radiation, the path of the radiation from the emitting areas or faces of the separate transmitters to the separate points in the field of measurement is of equal length and for this reason the separate points in the field of measurement will be homogeneously illuminated so that readings taken are generally valid and may be processed in the same way. A further point is that the lower limit to the intensity of the separate beams only has to have a low value so that one may be certain that any undesired thermal effect in the field of measurement or the sample to be examined is kept as low as possible. This being so, it becomes possible for the transmitters to be placed near the field of measurement without any danger of overly great thermal effects on the sample. It is for this reason that the reflectance measuring apparatus generally, or the reflectance measuring head as such, may be made small in size.

BRIEF DESCRIPTION OF THE DRAWING

The FIGURE illustrates the basic relationship between the transmitted light guide cable and the received light guide cable relative to the viewed surface and the diaphragm.

DETAILED DESCRIPTION OF THE PREFERRED EMBODIMENT

As part of a further development of the invention the separate transmitters are made up of the optic fiber guides of a transmitted light guide cable (S). The heating effect on the sample may then be even further cut down, inasfar as the light source may be spaced at some distance from the sample and/or inasfar as the radiation with a heating effect (in fact the IR components) is not let through by the optic guides or fibers.

In this respect the axis of the transmitted light guide cable (S) is preferably at a selected angle $\beta$ to a line normal to the area of the field of measurement and the inlet or entry plane (SF) of the transmitted light guide (S) is ground and polished or cut at this same angle $\beta$ so that in this way a very simple and space-saving design of the reflectance measuring apparatus becomes possible, if reflectance measuring heads of small size are desired. With this form of the invention one may be certain that the discrete rays or beams are directed to the field of measurement along the same light paths, that is to say distances.

As part of a further useful development of the invention the angle $\beta$ is in keeping with the equation $$n_i \sin \beta = \sin \sigma,$$

wherein $\sigma$ is the angle made between the axis of a radiation cone of an optic fiber guide and a line normal to the field of measurement and $n_i$ is the refractive index of the core material of the optic guide fibers, this being more specially the case for fibers with small exit radiation angles.

A further useful effect may be produced, if for receiving the radiation reflected by the field of measurement there is a received light guide cable (E) made up of a number of optic fibers. This makes possible an even more even processing of the reflected radiation with respect to the separate points of measurement.

It is best for the receiving areas or entry faces of the optic fiber guides to be placed in a plane that is parallel to the plane of the field of measurement. This design furthermore makes for more homogeneous processing of the field of measurement. The received light guide cable, made up of the single optic fiber guides, may best be so ground and polished that the inlet or entry face of the received light guide is parallel to the plane of the field of measurement. It is furthermore possible for the received light guide cable, whose receiving plane is normal to the axis of the received light guide cable, to be so placed that with respect to its middle axis the received light guide cable is normal to the plane of the field of measurement.

A simple structure of the reflectance measuring apparatus is more specially possible if the receiving face of the received light guide (E) and the transmitting face of the transmitted light guide (S) are in one and the same plane.

It is more specially if the received light guide cable is placed so that its middle or center axis is normal to the plane of the field of measurement that the received light guide cable may have its place taken by a received light guide rod or furthermore by a diaphragm system.

It is best for the field of measurement to be limited by a diaphragm (MB) with the desired area and form. It is with such a diaphragm that one may be certain that the marginal attenuation of the beams does not have undesired effects on the outcome of measurement. As a possible change in the system or in addition it is furthermore possible for the form of the transmitted light guide cable's emission face and/or the receiving face of the received light guide cable to have the same form as the measurement area. This is further step to make it possible for any desired form of area of measurement to be measured without any undesired effects on the outcome of measurement.

The emission area of face of the transmitted light guide and of the received light guide is best made greater or equal to the area of measurement, the effect of this being stopping marginal attenuation in intensity of the transmitted radiation beam and of the reflectance radiation having undesired effects on the outcome of measurement.

In keeping with another preferred form of the present invention the axes running through the geometrical middle points of the emission face of the transmitted light guide cable and of the receiving face of the received light guide cable come together at the geometrical middle point of the surface of measurement so that one may on the one hand be certain of a symmetrical illumination of the surface of measurement and on the other hand of symmetrically receiving the reflected light coming from the surface of measurement, while putting an end to marginal attenuation of the radiation, that would otherwise have an undesired effect on the measuring operation, that is to say on the outcome of measurement.

A further preferred development of the invention is possible in which the axis running through the geometrical middle or center point of the receiving area is a line, placed at a right angle to the surface of measurement, running through the geometrical middle point of the said surface. This simple structure furthermore makes for symmetrical receiving of the reflected radiation while putting an end to marginal attenuation so that even processing or evaluation of the field of measurement is made possible.

A further useful effect is to be had if the angle $\sigma$ between the axis of the radiation beam of the transmitters and the normal to the field of measurement is in substance made equal to 45°. For measurement of reflectance this is the preferred angle of incidence, the reflected radiation being measured in a direction normal to the reflectance area or surface (a so-called 45°-0° system). The other way round, it is furthermore possible for the system to be such that the discrete radiation beams of the transmitters are directed normally to the measurement area and for the reflected light to be received at an angle of 0° to 90° and more specially of 45°.

The aperture angle $\delta$ of the transmitted light guide fibers of the transmitted light guide cable is best made under 15° so as to get, as far as possible, dot-like cones of light or at least cones having a small diameter so that the field of measurement may be illuminated point for point with small light dots.

In keeping with a further preferred working example of the invention the aperture angle $\epsilon$ of the received light guide fibers is 30°. If the aperture angle $\delta$ of the transmitted light guide fibers is made less than 15° and the aperture angle $\epsilon$ of the received light guide fibers is made 30°, it is then possible, without any further developments, to make certain that there is no 45° reflection (complete reflection), that would otherwise have an undesired effect on the outcome of measurement.

A diaphragm is preferably placed on a glass plate G functioning as a support plate for the reflecting material.

An account will now be given of the invention using the single FIGURE herein by way of example.

The working example of which the account will now be given is a so-called 45°-0° system that is preferred for measuring reflectance and is furthermore noted in DIN Standards.

In this working example light guide cables are used for the transmitters and the receiver. The middle or center axis of the transmitted light guide cable S makes an angle of $\beta$ with a line normal to the plane of the field of measurement. The outlet or exit face SF of the transmitted light guide cable (S) is so ground and polished at this angle that the outlet face SF is parallel to the plane of the field of measurement. The middle or center axes of the beams coming from the sepatate light guide fibers of the transmitted light guide cable S go to the plane R of the field of measurement at an angle $\sigma$ of 45°.

The middle axis of the received light guide cable is at a right angle to the plane of the field of measurement and the inlet or entry face EF of the received light guide cable E is parallel to the plane of the field of measurement. In the present working example the outlet or exit face SF of the transmitted light guide cable SF and the inlet or entry face EF of the received light guide cable E are in one and the same plane. The form of the outlet face SF of the transmitted light cable S and/or of the inlet face EF of the received light guide cable E are selected to be in keeping with the form of the field R of measurement and in the other case in keeping with the form of the aperture MB. It is for this reason that marginal attenuation of the transmitted radiation beam and of the reflected light is by and large put an end to so that such marginal attenuation does not have any undesired effects on the outcome of the measuring operation. A further way of putting an end to marginal attenuation of the radiation is (as is the case in the present invention) to have the axes running through the geometrical middle points of the emission face of the transmitted light guide cable and of the inlet face of the received light guide cable meeting at point, that is the geometrical middle or center point of the plane of measurement.

This makes certain of a symmetrical form, that for its part makes possible even processing or evaluation of the separate single points of the field of measurement while stopping marginal attenuation having effects on the outcome of measurement or readings taken.

The emission face SF of the transmitted light guide cable S and/or the receiving face EF of the received light guide cable E are best at least two times as great as the area of the field of measurement, that may be limited by an aperture MB.

In the present case the emission face SF, the receiving face EF and the face or area of the field of measurement R are round. However such areas may have another form, although a useful effect is to be had if the surfaces or areas have the same form.

It would naturally furthermore be possible for the transmitted light guide cable in the present form of the invention to have its place taken by the received light guide cable and the other way round.

I claim:

1. In an apparatus for measuring reflectance at a reflecting surface placed in a field of measurement, comprising a transmitted light guide cable made up of a number of light guide fibers for emission of a plurality of discrete beams along a transmitted light cone axis and a received light guide cable made up of a number of light guide fibers for receiving radiation reflected from said field of measurement along a received light cone axis, the light guide fibers of the transmitted and received light guide cables having transmitting and inlet faces respectively, the transmitted and received light cone axes passing through geometrical middle points of the respective transmitting and inlet faces, said transmitting faces of the transmitted light guide fibers and said inlet faces of the received light guide fibers being positioned in planes parallel to the plane of said field of measurement, the transmitted and received light cone axes meeting at a geometrical middle point of the surface to be measured, the transmitting face of the transmitted light guide cable and the inlet face of the received light guide cable having a form the same as the form of the surface to be measured, the transmitted and received light guide cables having aperture angles of less than 15° and 30+ respectively.

2. The apparatus as claimed in claim 1 wherein the said transmitted light guide cable is so placed that an axis thereof is at a selected angle to a line normal to said field of measurement, said transmitting faces of the said transmitted light guide fibers being ground and polished at this said selected angle.

3. The apparatus as claimed in claim 2 wherein said selected angle is equal to $\beta$ that is given by the equation $$n_i \sin \beta = \sin \sigma$$

wherein $\sigma$ is the angle between the axis of a light cone of a light guide fiber and the said line normal to the field of measurement and $n_i$ is the index of refraction of core material of said light guide fibers.

4. The apparatus as claimed in claims 1 or 2 or 3 wherein the inlet faces of the received light guide fibers and a transmitting face of the transmitting light guide cable being in one and the same plane.

5. The apparatus as claimed in claim 1 further comprising a diaphragm for limiting the field of measurement to an area no greater than either the transmitting face or the inlet face.

6. The apparatus as claimed in claim 1 wherein said received light cone axis of the received light guide cable is a line normal to the surface to be measured.

7. The apparatus as claimed in claim 1 wherein an angle between an axis of the transmitted beam and a line normal to the field of measurement is in substance equal to 45°.

8. The apparatus as claimed in claim 5 further comprising a glass plate with said diaphragm thereon, said glass plate functioning as a support face for reflecting material.

9. The apparatus as claimed in claims 1 or 5 wherein said transmitting face of the transmitted light cable is at least equal in size to the size of the surface to be measured.

10. The apparatus as claimed in claim 9 wherein said receiving face of the received light guide cable is at least equal in size to the size of the surface to be measured.

11. The apparatus as claimed in claim 1 wherein said transmitted light guide cable has its place taken by said received light guide cable and said received light guide cable has its place taken by said transmitted light guide cable.

12. In an apparatus for measuring reflectance at a reflecting surface placed in a field of measurement, comprising a transmitted light guide cable made up of a number of light guide fibers for emission of a plurality of discrete beams and a received light guide cable made up of a number of light guide fibers for receiving radiation reflected from said field of measurement, the light guide fibers of the transmitted and received light guide cables having transmitting and inlet faces respectively, said transmitting faces of the transmitted light guide fibers and said inlet faces of the received light guide fibers being positioned in planes parallel to the plane of said field of measurement so the transmitting face of the transmitted light guide cable and the receiving face of the received light guide cable have a form the same as the form of the surface to be measured, a glass plate acting as a support face for the reflecting surface, and a diaphragm, mounted to the glass plate, for limiting the field of measurement to a chosen size, the chosen size being equal to or smaller in area than either the transmitting face or the inlet face.

* * * * *